(12) United States Patent
Vaidya et al.

(10) Patent No.: US 8,801,832 B2
(45) Date of Patent: Aug. 12, 2014

(54) SOUR GAS AND ACID NATURAL GAS SEPARATION MEMBRANE PROCESS BY PRE REMOVAL OF DISSOLVED ELEMENTAL SULFUR FOR PLUGGING PREVENTION

(71) Applicant: Saudi Arabian Oil Company, Dhahran (SA)

(72) Inventors: Milind M. Vaidya, Dhahran (SA); Jean-Pierre R. Ballaguet, Dhahran (SA); Sebastien A. Duval, Dhahran (SA); Anwar H. Khawajah, Dammam (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 14/178,936

(22) Filed: Feb. 12, 2014

(65) Prior Publication Data

US 2014/0187838 A1    Jul. 3, 2014

Related U.S. Application Data

(62) Division of application No. 13/975,935, filed on Aug. 26, 2013, now Pat. No. 8,696,791, and a division of application No. 12/916,701, filed on Nov. 1, 2010, now Pat. No. 8,540,804.

(51) Int. Cl.
    *B01D 53/14*    (2006.01)
(52) U.S. Cl.
    USPC ............... 95/8; 95/11; 95/92; 95/94; 95/195; 95/196; 95/205; 95/24; 95/229; 95/235

(58) Field of Classification Search
    None
    See application file for complete search history.

(56) References Cited

U.S. PATENT DOCUMENTS

| 2,881,047 | A | 4/1959 | Townsend |
| 3,170,766 | A | 2/1965 | Townsend |
| 3,534,528 | A | 10/1970 | Porter |
| 3,909,422 | A | 9/1975 | Sample |
| 4,239,630 | A | 12/1980 | Atkinson et al. |
| 4,290,900 | A | 9/1981 | Sharp et al. |
| 4,444,571 | A | 4/1984 | Matson |

(Continued)

FOREIGN PATENT DOCUMENTS

| DE | 3315930 A1 | 3/1984 |
| WO | 20080027381 A2 | 3/2008 |

OTHER PUBLICATIONS

English Patent Abstract of DE3315930 from Espacenet.com, published Mar. 1, 1984 (2 Pages).

(Continued)

*Primary Examiner* — Duane Smith
*Assistant Examiner* — Pankti Patel
(74) *Attorney, Agent, or Firm* — Bracewell & Giuliani LLP; Constance G. Rhebergen; James M. Sellers

(57) ABSTRACT

Methods for removing sulfur from a gas stream prior to sending the gas stream to a gas separation membrane system are provided. Two schemes are available. When the sulfur content is high or flow is relatively high, a scheme including two columns where one tower is regenerated if the sulfur concentration exceeds a preset value can be used. When the sulfur content is low or flow is relatively low, a scheme including one column and an absorption bed.

5 Claims, 3 Drawing Sheets

(56) References Cited

U.S. PATENT DOCUMENTS

| | | | |
|---|---|---|---|
| 4,608,060 A | 8/1986 | Kulprathipanja et al. | |
| 4,710,204 A | 12/1987 | Kraus et al. | |
| 4,804,485 A | 2/1989 | Carroll et al. | |
| 4,857,078 A * | 8/1989 | Watler | 95/50 |
| 4,881,953 A | 11/1989 | Prasad et al. | |
| 5,028,343 A | 7/1991 | Lindstrom | |
| 5,104,557 A | 4/1992 | Lindstrom | |
| 5,306,331 A | 4/1994 | Auvil et al. | |
| 5,306,476 A | 4/1994 | Jalan et al. | |
| 5,401,300 A | 3/1995 | Lokhandwala et al. | |
| 5,407,466 A | 4/1995 | Lokhandwala et al. | |
| 5,407,467 A | 4/1995 | Lokhandwala et al. | |
| 5,556,449 A | 9/1996 | Baker et al. | |
| 5,558,698 A | 9/1996 | Baker et al. | |
| 5,585,334 A | 12/1996 | Shaw | |
| 5,772,733 A | 6/1998 | Lokhandwala et al. | |
| 6,361,582 B1 | 3/2002 | Pinnau et al. | |
| 6,361,583 B1 | 3/2002 | Pinnau et al. | |
| 6,383,257 B1 | 5/2002 | McDermott et al. | |
| 6,565,626 B1 | 5/2003 | Baker et al. | |
| 6,572,679 B2 * | 6/2003 | Baker et al. | 95/47 |
| 6,579,341 B2 | 6/2003 | Baker et al. | |
| 6,592,650 B2 | 7/2003 | Pinnau et al. | |
| 6,723,152 B2 | 4/2004 | Bikson et al. | |
| 6,896,717 B2 | 5/2005 | Pinnau et al. | |
| 6,946,209 B1 | 9/2005 | Israelson | |
| 7,452,405 B2 * | 11/2008 | Duraiswamy et al. | 95/45 |
| 2005/0022668 A1 * | 2/2005 | Cairns | 95/226 |
| 2005/0135983 A1 * | 6/2005 | Geosits et al. | 423/242.1 |
| 2007/0280868 A1 * | 12/2007 | Cisneros | 423/220 |
| 2009/0317316 A1 | 12/2009 | Mclauchlan et al. | |
| 2011/0033370 A1 | 2/2011 | Ayala et al. | |
| 2012/0103185 A1 | 5/2012 | Vaidya et al. | |

OTHER PUBLICATIONS

International Search Report and Written Opinion issued in Application No. PCT/US2011/057801, dated Jan. 25, 2012 (12 Pages).

* cited by examiner

SOUR GAS AND ACID NATURAL GAS SEPARATION MEMBRANE PROCESS BY PRE REMOVAL OF DISSOLVED ELEMENTAL SULFUR FOR PLUGGING PREVENTION

CROSS-REFERENCE TO RELATED APPLICATIONS

This patent application is a divisional application of U.S. patent application Ser. No. 12/916,701, filed on Nov. 1, 2010, now U.S. Pat. No. 8,540,804, and a divisional application of U.S. patent application Ser. No. 13/975,935, filed on Aug. 26, 2013. For purposes of United States patent practice, this application incorporates the contents of the prior Applications by reference in their entirety.

FIELD OF THE INVENTION

This invention relates to methods for removing sulfur from gas streams prior to sending the gas streams to gas separation membranes.

BACKGROUND OF THE INVENTION

Natural gas streams can contain dissolved elemental sulfur and release it in the casing or downstream the well head if subjected to changes in composition, temperature, or pressure. In the case of gas separation membranes, gas separation is based on the ability of a thin polymer layer to discriminate molecules either on their size or their solubility. Irrelevant of the mechanism used in permeation, a change in gas composition and pressure can occur. The change in pressure also generally induces a cooling effect that also induces a change in temperature. Depending upon the gas composition, pressure, and temperature, the dissolved elemental sulfur in natural gas could deposit in the membrane module due to the intrinsic changes in gas composition, pressure, and temperature in the membrane separation process. Indeed, retentate and permeate streams exhibit lower solubility of sulfur than feed and this phenomenon leads to sulfur deposition within the membrane system resulting either in a blockage or membrane module breakage and finally discontinuity in the operation.

Membrane based gas separation is also a well-known process used to remove or concentrate $H_2S$, $CO_2$, $H_2$, $CO$, $N_2$, and $O_2$ from streams. Polymeric gas membrane systems have been used in refineries, petrochemical plants, natural gas fields, and the like. The preferred membranes for many applications are those systems have been used offering high selectivity and fluxes. For example, U.S. Pat. Nos. 6,572,679; 6,361,583; 6,361,582; 6,723,152; 6,579,341; 6,565,626; 6,592,650; and 6,896,717 describe the chemistry of such membrane systems and processes that demonstrate their performance.

Several types of technology exist for absorbing or removing sulfur from streams. For example, the technology and the solvent chemistry to selectively absorb sulfur in natural gas stream are well known in the art. For instance, U.S. Pat. Nos. 5,028,343; 5,585,334; 4,804,485; and WO 2008/027381 describe solvent chemistry that can selectively absorb sulfur in natural gas streams. These solvents can be refreshed or changed when the load in sulfur impairs a proper absorption of sulfur for given flows and contactor design. The sulfur content in the solvent is also well known in the art, and an on-line measurement system is preferred such as on line X-ray fluorescence technique.

As another technology used to separate sulfur from a gas stream, sulfur solubility in hydrocarbon, carbon dioxide and hydrogen sulfide gas mixture has been investigated by others An example process using this type of technology is described in U.S. Pat. No. 6,565,626.

U.S. Pat. Nos. 5,401,300; 5,407,467; and 5,407,466 describe only sour gas treatment processes for removal of $H_2S$, but not the dissolved sulfur in natural gas. U.S. Pat. No. 5,585,334 describes the dissolution of sulfur from the sulfur deposits and sulfur plugs in gas wells, oil wells, vessels or conduits for transporting fluids containing sulfur.

Although many patents describe processes for removing $H_2S$ or sulfur from gas streams, a need exists for processes to help prevent sulfur deposition in gas separation membrane systems. It would be advantageous if the processes could prevent loss of production, as well.

SUMMARY OF THE INVENTION

In view of the foregoing, a sour natural gas separation membrane process is provided in which natural gas is first passed through a solvent scrubber to selectively absorb elemental sulfur in natural gas stream and then passed through a coalescing filter to remove entrained liquid droplets before passing the natural gas through gas separation membranes. These solvents can be refreshed or changed when the load in sulfur impair a proper absorption of sulfur for given flows and contactor design. Once the solvent becomes saturated, the solvent can be changed. The sulfur content and solubility of sulfur in the solvent is well documented in the art. Setting a cleaning frequency is difficult because the sulfur content in gas can vary due to changes in process conditions upstream of the unit. To alleviate this problem, an on-line measurement system can be used, such as on line X-ray fluorescence technique, to predict the amount of sulfur in the natural gas to determine when the solvent scrubber needs to be regenerated or changed.

More specifically, methods of removing sulfur from a gas stream are provided as embodiments of the present invention. In an embodiment of the present invention, a method of removing sulfur from a gas stream is provided. In this embodiment, the gas stream is contacted with a solvent to selectively absorb at least a portion of elemental sulfur from the gas stream such that the gas stream has a sulfur concentration that is substantially less than prior to the gas stream being contacted with the solvent. Entrained liquid droplets are then filtered and coalesced from the gas stream so that the elemental sulfur does not become deposited on a gas separation membrane. The gas stream is then passed through the gas separation membrane. This embodiment of the present invention is particularly useful when the sulfur concentration in the gas stream is relatively high.

Another method of removing sulfur from a gas stream is provided as another embodiment of the present invention. In this embodiment, the gas stream is contacted with a solvent to selectively absorb at least a portion of elemental sulfur from the gas stream. The entrained liquid droplets are then filtered and coalesced from the gas stream. The gas stream is then passed through gas separation membranes. In this embodiment, one absorber is in use and the second one in regeneration for a continuous process. A gas stream sulfur concentration of an overhead stream of the solvent of an exhaust/exit gas from the scrubber is then analyzed and the gas stream is sent to a second column if the sulfur concentration exceeds the sulfur solubility estimated in the retentate and permeate flows by membrane separation process simulation including the provision for inaccurate measurements and estimation.

The solvent scrubber that is not in use is regenerated by sending a gas capable of dissolving sulfur through the solvent scrubber. This embodiment of the present invention is particularly useful when the sulfur concentration in the gas stream is relatively high.

As yet another embodiment of the present invention, a method of removing sulfur from a gas stream is provided. In this embodiment, the gas stream is cooled enable removing liquid in a knockout drum and hence producing a gas stream without liquids while entering the membrane module. The gas stream is then contacted with a solvent to selectively absorb at least a portion of elemental sulfur from the gas stream. The gas stream without liquids is contacted with an absorbent bed to removed sulfur in excess of solubility. A gas stream sulfur concentration in the gas stream without liquids is then analyzed to determine if the sulfur concentration exceeds the sulfur solubility estimated in the retentate and permeate flows by membrane separation process simulation including the provision for inaccurate measurements and estimation. The gas stream without liquids is then passed through gas separation membranes. This embodiment of the present invention is particularly useful when the sulfur concentration in the gas stream is relatively low or the gas stream flow rate is relatively low.

Embodiments of the present invention alleviate many of the drawbacks associated with prior art systems by providing a pre-conditioning treatment of the gas stream by flowing the gas stream in a sulfur solvent contactor that will prevent both sulfur deposit and loss of production. As a consequence, the gas separation by membrane technology is more reliable and can offer a higher life expectancy.

BRIEF DESCRIPTION OF THE DRAWINGS

So that the manner in which the above-recited features, aspects and advantages of the invention, as well as others that will become apparent, are attained and can be understood in detail, more particular description of the invention briefly summarized above can be had by reference to the embodiments thereof that are illustrated in the drawings that form a part of this specification. It is to be noted, however, that the appended drawings illustrate some embodiments of the invention and are, therefore, not to be considered limiting of the invention's scope, for the invention can admit to other equally effective embodiments.

DETAILED DESCRIPTION OF THE INVENTION

Figure 1:
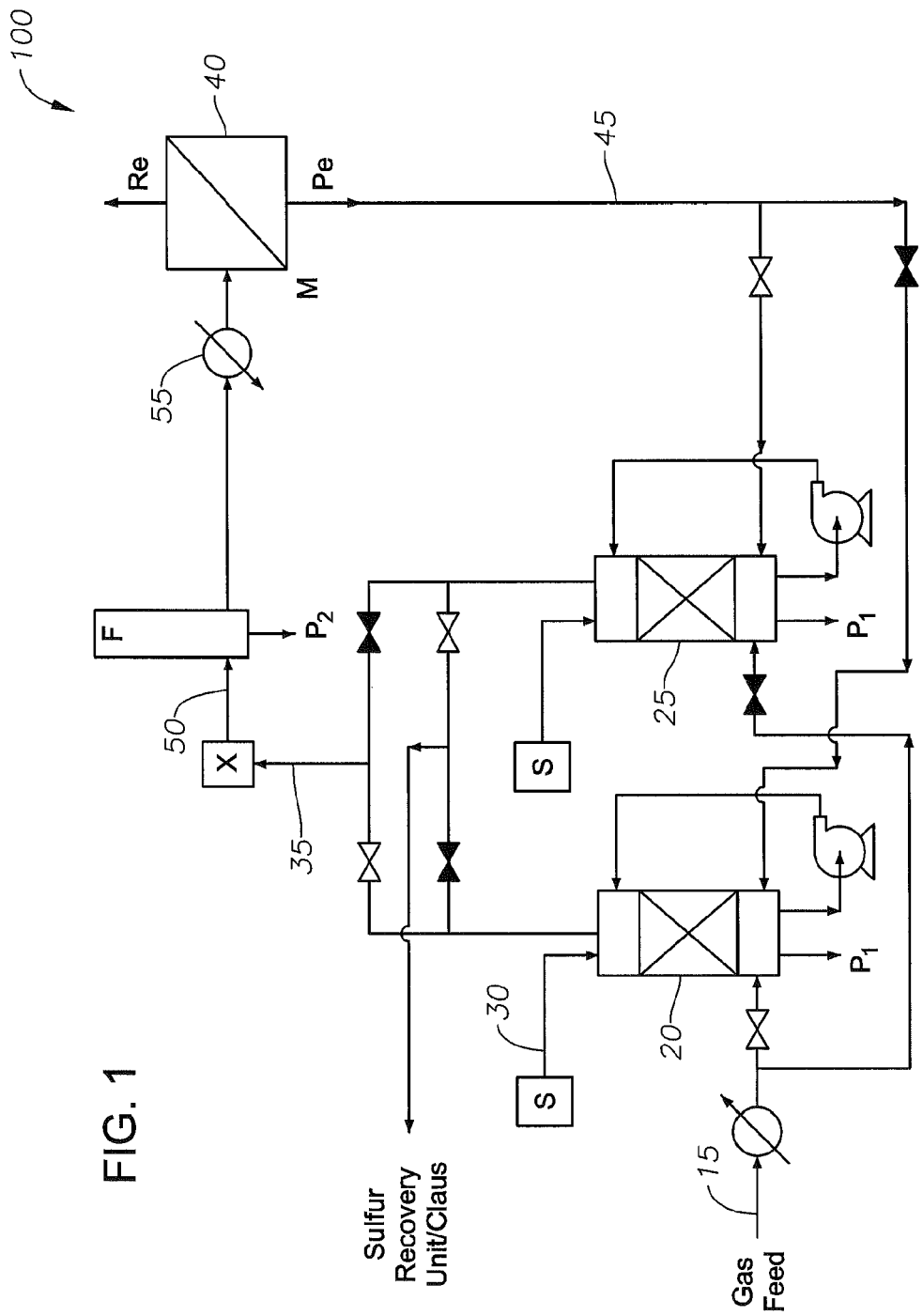
FIG. 1 provides a schematic diagram of one embodiment of the present invention that can be used when a high concentration of sulfur is present in the gas stream.

Although the following detailed description contains many specific details for purposes of illustration, it is understood that one of ordinary skill in the art will appreciate that many examples, variations and alterations to the following details are within the scope and spirit of the invention. Accordingly, the exemplary embodiments of the invention described herein and provided in the appended figures are set forth without any loss of generality, and without imposing limitations, relating to the claimed invention.

Embodiments of the present invention include methods that can be used to pre-condition a gas stream by flowing the gas stream in a sulfur solvent contactor that will prevent both sulfur deposition on downstream equipment and subsequent loss of production. The use of the methods of the present invention are particularly advantageous when used in combination with gas separation membrane systems. As a consequence of using the methods of the present invention, the gas separation by membrane technology is more reliable and offers a higher life expectancy than without the pre-conditioning of the gas stream.

In an embodiment of the present invention, a method of removing sulfur from a gas stream is provided. In this embodiment, the gas stream is contacted with a solvent to selectively absorb at least a portion of elemental sulfur from the gas stream such that the gas stream has a sulfur concentration that is substantially less than prior to the gas stream being contacted with the solvent. Entrained liquid droplets are then filtered and coalesced from the gas stream so that the sulfur does not become deposited on a gas separation membrane. The gas stream is then passed through a gas separation membrane. This embodiment of the present invention is particularly useful when the sulfur concentration in the gas stream is relatively high.

In embodiments of the present invention, the step of contacting the gas stream with a solvent can occur in a solvent scrubber. In an aspect, the step of contacting the gas stream with a solvent can occur when the gas stream is flowing upstream and the solvent is flowing downstream counter currently to the gas stream.

Various types of process equipment can be used when filtering entrained liquid droplets from the gas stream. In an aspect, the step of filtering entrained liquid droplets can occur in a coalescing filter. Other suitable types of process equipment that are capable of filtering the entrained liquid droplets will be apparent to those of skill in the art and are to be considered within the scope of the present invention.

In embodiments of the present invention, the methods of removing sulfur from a gas stream can also include the step of regenerating the solvent scrubber by sending a gas capable of dissolving sulfur through the solvent scrubber. In an aspect, the gas capable of dissolving sulfur comprises hydrogen sulfide recovered from the gas separation membrane. Besides hydrogen sulfide, acid rich gases generated from the acid gas removal system (i.e., amine treatment) can also be used to dissolve sulfur. Other suitable types of gases that are capable of dissolving sulfur will be apparent to those of skill in the art and are to be considered within the scope of the present invention.

Besides regenerating the solvent, a continuous filtering system could be used to remove sulfur from the gas stream. Other suitable methods for removing sulfur from the gas stream will be apparent to those of skill in the art and are to be considered within the scope of the present invention.

The operating parameters of the equipment can be varied depending upon the concentration of sulfur in the stream. Other process conditions can also affect the suitable operating conditions for the processes described in the present invention. For example, in an aspect, the step of regenerating the solvent scrubber can occur at any pressure that is capable of compensating for the pressure loss in the regeneration tower and/or piping. As another example, the step of contacting the gas stream with the solvent occurs at a pressure substantially similar to a feed gas pressure of the gas stream. Other suitable operating pressures can be used, as will be apparent to those of skill in the art, and are to be considered within the scope of the present invention.

In an aspect, the solvent regeneration gas comprises hydrogen sulfide. Other suitable solvent regeneration gases will be apparent to those of skill in the art and are to be considered within the scope of the present invention.

As the solvent continues to contact the gas stream, the sulfur content in the solvent continues to increase. Once the sulfur content of the solvent exceeds a preset value, the solvent scrubber should be regenerated. Various methods exist for determining the concentration of sulfur contained in the overhead exit gas stream as it exits the solvent scrubber. In embodiments of the present invention, the methods of removing sulfur from a gas stream can also include analyzing a gas stream sulfur concentration of an overhead exit stream of the solvent scrubber and sending the gas stream to a second column if the sulfur concentration exceeds the sulfur solubility estimated in the retentate and permeate flows by membrane separation process simulation including the provision for inaccurate measurements and estimation. In an aspect, an X-ray analyzer can be used to measure the sulfur content of the overhead/exit stream. In other aspects, raman-laser or gas chromatography with a sulfur sensor can be used to measure the sulfur content of the overhead/exit stream. Other suitable methods of measuring the sulfur content of the overhead/exit stream will be apparent to those of skill in the art and are to be considered within the scope of the present invention.

Another method of removing sulfur from a gas stream is provided as an embodiment of the present invention. In this embodiment, the gas stream is contacted with a solvent to selectively absorb at least a portion of elemental sulfur from the gas stream. The entrained liquid droplets are then filtered and coalesced from the gas stream the sulfur does not become deposited on a gas separation membrane. The gas stream is then passed through the gas separation membrane. In this embodiment, one absorber is in use and the second one is in regeneration for a continuous process. A gas stream sulfur concentration of an overhead stream of the solvent scrubber is then analyzed and the gas stream is sent to a second column if the sulfur concentration exceeds the sulfur solubility estimated in the retentate and permeate flows by membrane separation process simulation including the provision for inaccurate measurements and estimation. The solvent scrubber not in use is regenerated by sending a gas capable of dissolving sulfur through the solvent scrubber. This embodiment of the present invention is particularly useful when the sulfur concentration in the gas stream is relatively high.

The process 10 shown in FIG. 1 can be utilized and is preferred when the concentration of sulfur in the gas stream 15 and or flow to be treated is high. For purposes of FIG. 1, S=solvent; $P_1$, $P_2$=purges; X=$X_{ray}$-sulfur concentration; F=filter-coalescer; M=membrane unit; Re=retentate; and Pe=permeate. This embodiment typically includes two towers 20, 25 and is operated as a continuous process.

Solvent 30 in the first tower 20 absorbs the sulfur from the gas stream 15 while the second solvent tower 25 is used in a regeneration step. These are two separate systems operating in embodiments of the present invention. In the first system, the absorption tower 20 operates at feed gas pressure, while the regeneration tower 25 in the second system operates at low pressure. The gas stream 15 flows upstream in the absorption tower 20, which is equipped with packings or trays. The gas stream 15 can be sent to a chiller prior to the absorption tower 20 to limit the quantity of entrained liquid in the gas stream 15 and to maximize the solvent absorption of sulfur in the gas stream 15, if needed. The solvent 30 flows downstream counter currently to the gas stream 15, which absorbs the sulfur contained in the gas stream 15. The solvent 30 sulfur loading increases along the run. An on-line analyzer X (X-ray for example) allows measuring the sulfur concentration in the exit gas stream 35 at the exit of the absorption column 20 and before the membrane unit 40. The analyzer X can send an alarm as soon as the sulfur content in the exit gas stream 35 exceeds a preset value. The preset value can be the sulfur solubility estimated in the retentate and permeate flow streams by membrane separation process simulation including the provision for inaccurate measurements and estimation. The maximum amount of sulfur that can be present is the amount that enables sulfur absorption to prevent the sulfur concentration in the overhead gas to exceed the sulfur solubility in retentate and permeate flow streams. In an aspect, the amount of sulfur in the exit gas stream 35 can range from less than about 1 ppmV to about 350 ppmV.

If the sulfur content of the exit stream 35 exceeds the preset value, the gas feed 15 is then sent to the second column 25 while the first absorption column 20 is subjected to regeneration mode. In the regeneration mode at low pressure, the $H_2S$ concentrated gas stream 45 separated in the membrane unit 40 is used to recover the sulfur from the loaded solvent 30. $H_2S$ is well known as an efficient solvent for elemental sulfur. The $H_2S$ and sulfur gas stream will then be treated by a classical recovery unit, such as a Claus process that is eventually followed by a tail gas unit for extreme sulfur recovery. Other suitable methods for recovering sulfur, such as precipitation, filtration, and the like, will be apparent to those of skill in the art and are to be considered within the scope of the present invention.

A new cycle for the two columns 20, 25 begins as soon as the sulfur concentration in the exit gas stream 35 arriving at the analyzer X exceeds the pre-set value. Other components, such as water and heavy hydrocarbons, will also be absorbed to a certain extent by the solvent 30. Periodically, a purge P is sent to a three phase separator and lost solvent is replaced by fresh solvent from the solvent tank S. The gas stream 50 with very low sulfur content is then treated in the membrane unit 40. In the membrane unit 40, the gas stream 50 goes to a filter-coalescer F to remove droplets of entrained liquids, solvent and some water in the purge P followed by heat exchanger 55. Heat exchanger 55 can reheat the gas stream 50, if needed, to ensure a gaseous stream is sent to the membrane module M. Separation of methane from other components, such as $N_2$, $H_2S$, $CO_2$, $H_2O$, $C_2^+$, and the like, takes place in membrane modules M. More concentrated gases exit the unit as permeate stream Pe and retentate stream Re for further processing in the gas plant.

Various types of solvents can be used in embodiments of the present invention. In an aspect, the solvent is polyethylene glycol, ethers of polyethylene glycol, polypropylene glycol, ethers of propylene glycol, n-methylpyrolidone, n-ethyl pyrolidone, n-cyclohexyl pyrolidone, n-phenyl morpholine, n-cyclohexyl morpholine, dimethyl disulfur, dimethyl-sulfur, carbon disulfide, xylene, toluene, BTX (mixture of benzene, toluene, and xylene), kerosene, naphthalene, alkyl-naphthalene, or combinations thereof. The solvent can be a member of the glycol family, such as polyethylene glycol, polypropylene glycol, and their related ethers (methyl, ethyl, etc.). The solvent can be a member of the pyrolidone family, such as N-methyl pyrolidone, N-ethyl pyrolidone, N-cyclohexyl pyrolidone, combinations thereof, and the like. The solvent can be a member of the morpholine family, such as n-phenyl morpholine, n-cyclohexyl morpholine, combinations thereof, and the like. The solvent can include an organic sulfur solvents, such as dimethyl-di-sulfur, dimethyl-sulfur, carbon disulfide, or be a sulfur containing solvent having the formula R—Sn—R, wherein R can be hydrocarbyl radical from 1 to 30 carbons, or alternatively, from 2 to 10 carbons, or alternatively, from 2 to 5 carbons. Other suitable organic solvents can include xylene, toluene, BTX, kerosene, naphthalene, alkyl-naphthalene, and the like. Other suitable types of solvents that can be used in embodiments of the present invention will be apparent to those of skill in the art and are to be considered within the scope of the present invention.

The size of the absorption tower 20 can vary depending upon the anticipated flowrate of the gas stream 15, as will be apparent to those of skill in the art. The absorbent tower 20 can also be used to reclaim the solvent solution periodically and then on a bypass of the second tower 25.

Figure 2:
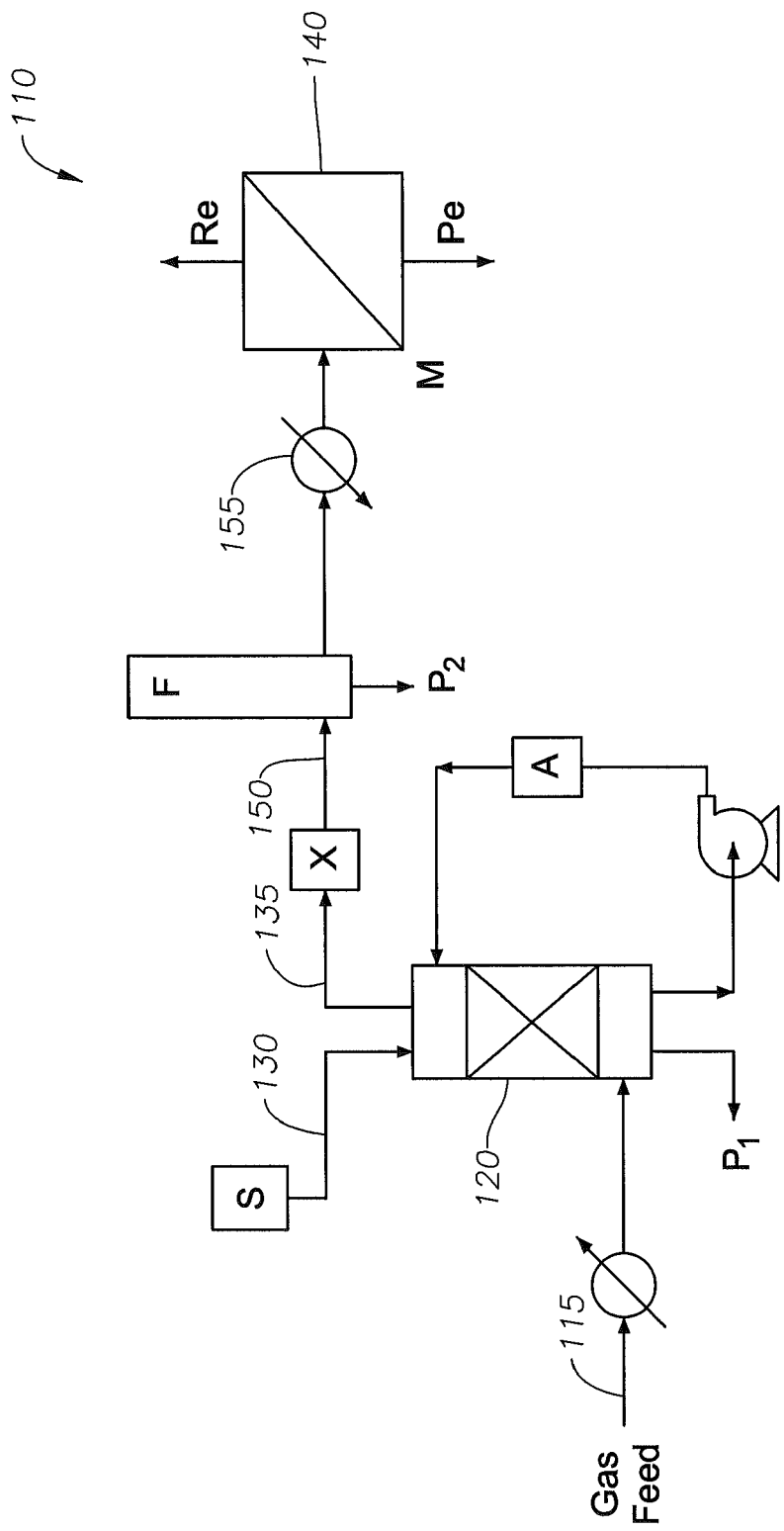
FIG. 2 provides a schematic diagram of one embodiment of the present invention that can be used when a low concentration of sulfur is present in the gas stream or if the gas stream has a low flow rate.

As yet another embodiment of the present invention, as shown in FIG. 2, a method of removing sulfur from a gas stream is provided. In this embodiment, the gas stream is cooled to enable removing liquid in a knockout pot and hence producing a gas stream without liquids while entering the membrane module M. The gas stream is then contacted with a solvent to selectively absorb at least a portion of elemental sulfur from the gas stream. The gas stream without liquids is contacted with an adsorbent or a filter to remove sulfur in excess of solubility. A sulfur concentration in the gas stream without liquids is then analyzed to determine if the sulfur concentration exceeds the sulfur solubility estimated in the retentate and permeate flows by membrane separation process simulation including the provision for inaccurate measurements and estimation. The gas stream is sent to a heat exchanger followed by a filter-coalescer to remove droplets of entrained liquids. The gas stream without liquids is heated in heat exchanger, if needed, to ensure a gaseous stream is sent to the membrane modules. The gas stream without liquids is then passed through gas separation membranes M.

The process 110 shown in FIG. 2 can be utilized when the concentration of sulfur in the gas stream 115 and or flow to be treated is low. With respect to FIG. 2, S=solvent; $P_1$, $P_2$=purges; X=Xray-sulfur concentrations; A=adsorbent; F=filter-coalescer; M=membrane unit; Re=retentate; and Pe=permeate.

More specifically, in the process 110 shown in FIG. 2, the gas stream 115 flows upstream in a column 120 equipped with packings or trays. The solvent 130 flows downstream counter currently to the gas stream 115 and absorbs the sulfur contained in the gas stream 115. Then the loaded solvent 130 is pumped, chilled and passes through a bed of adsorbent A where the sulfur in excess of solubility is trapped. Alternatively, a filter could be used instead of adsorbent A after precipitation of sulfur due to the temperature decrease. The adsorbent containing sulfur is periodically removed and replaced, which is considered as a waste. An on-line analyzer X (X-ray for example) allows measuring the sulfur concentration in the exit gas stream 135 before it is sent to the membrane unit 140. The analyzer X can send an alarm for adsorbent replacement as soon as the sulfur content exceeds the sulfur solubility estimated in the retentate and permeate flows by membrane separation process simulation including the provision for inaccurate measurements and estimation. Other components like water and heavy hydrocarbons will also be absorbed to a certain extent by the solvent 130. Periodically, purges $P_1$ and $P_2$, can be sent to a three phase separator and can be replaced by fresh solvent from the solvent tank S. Heavy HC can be recovered from the purges $P_1$ and $P_2$ in a three way separator. The gas stream 150 with very low sulfur content is then treated in the membrane unit 140. In the membrane unit 140, the gas stream 150 is sent to a filter-coalescer F to remove any entrained liquid droplets, solvent and some water in the purge P followed by a heat exchanger 155. Separation of methane from other components, such as $N_2$, $H_2S$, $CO_2$, $H_2O$, $C_2^+$, and the like, takes place in membrane modules M. More concentrated gases exit the unit as permeate stream Pe and retentate stream Re for further processing in the gas plant.

Various types of adsorbent materials can be used in embodiments of the present invention. In an aspect, the adsorbent bed contains activated carbon, supported metallic oxides, supported organic oxides, or combinations thereof. Other suitable types of adsorbent materials that can be used in embodiments of the present invention will be apparent to those of skill in the art and are to be considered within the scope of the present invention. When a filter is used to remove sulfur from the loaded solvent 130, the filter can include supported metallic filters, supported organic filters, polymeric filters, or combinations thereof. Other suitable types of filters that can be used in embodiments of the present invention will be apparent to those of skill in the art and are to be considered within the scope of the present invention.

As an advantage of the present invention, the frequency of regenerating the solvent scrubber can be easily determined. Setting cleaning frequency based upon other factors, such as run time, is difficult because the sulfur content in the gas stream can vary due to changes in process conditions upstream of the unit. Sampling can also be used to monitor solvent regeneration frequency. Use of an on-line measurement system, such as on line X-ray fluorescence technique, as used in embodiments of the present invention, can be utilized to determine the amount of sulfur in the gas stream to determine the frequency in which the solvent scrubber should be regenerated.

EXAMPLE

Prior art processes used to removed sulfur from streams do not describe or take into account gas membrane separation processes and ways to prevent the sulfur deposition within the membrane system resulting either in a blockage or membrane module breakage, eventual discontinuity in the operation membrane separation process, and loss of production arising due to solubility evolution along membrane separation process.

Polymeric membrane based gas separation has been used in refineries, petrochemical plants, natural gas fields, and the like. The preferred membranes for many applications are the ones offering high selectivity and fluxes. For example, U.S. Pat. Nos. 6,572,679; 6,361,583; 6,361,582; 6,723,152; 6,579,341; 6,565,626; 6,592,650; and 6,896,717 describe the chemistry of such membrane gas separation processes.

Sulfur solubility in hydrocarbon, carbon dioxide, and hydrogen sulfide gas mixture has been investigated by others. In the present invention, simulation models were developed to assess the amount of sulfur that can be dissolved in a gas mixture for a given composition, pressure, and temperature.

Figure 3:
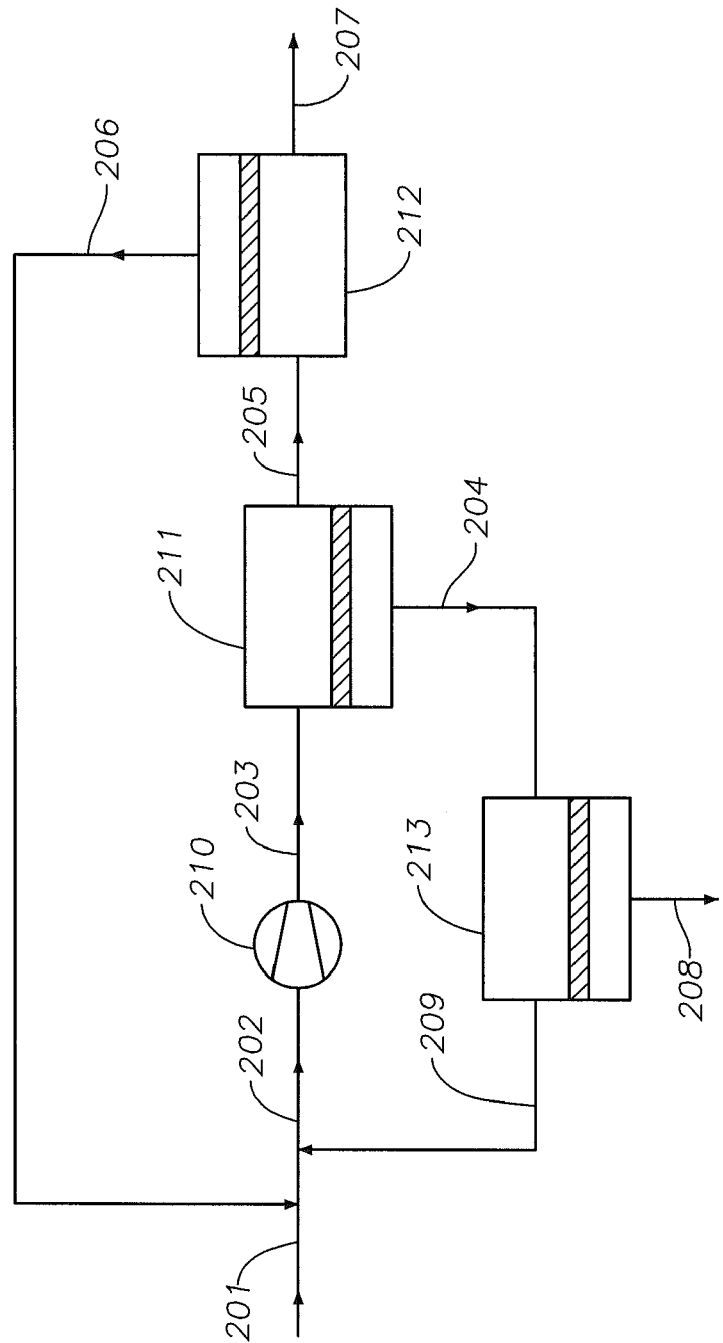
FIG. 3 provides a schematic diagram that is FIG. 4 of U.S. Pat. No. 6,565,626, which is in accordance with prior art embodiments.

The membrane gas separation scheme shown in FIG. 3 is from U.S. Pat. No. 6,565,626 (hereinafter "the '626 patent"). Table 26 of the '626 patent is also included which provides example operating conditions for the process shown in FIG. 3. Table 26 shows the gas composition for feed, permeate, and retentate streams for different stages. Tables 1 and 2 contain the data, sulfur solubility and maximal sulfur concentration for the different streams obtained by the simulation models developed in accordance with embodiments of the present invention.

TABLE 26

| | Stream | | | | | | | | |
|---|---|---|---|---|---|---|---|---|---|
| | 201 | 202 | 203 | 204 | 205 | 206 | 207 | 208 | 209 |
| Flow (MMscfd) | 10.0 | 14.2 | 14.2 | 6.2 | 8.0 | 1.2 | 6.8 | 3.2 | 3.0 |
| Temp. (° C.) | 50 | 38 | 25 | 16 | 7 | 4 | 2 | 13 | 10 |
| Pressure (psia) | 200 | 200 | 1,200 | 200 | 1,200 | 200 | 1,200 | 20 | 200 |
| Component (mol. %): | | | | | | | | | |
| Nitrogen | 5.0 | 5.3 | 5.3 | 7.4 | 3.7 | 6.5 | 3.2 | 8.8 | 5.8 |
| Methane | 80.0 | 83.5 | 83.5 | 68.9 | 94.8 | 88.2 | 96.0 | 46.0 | 93.2 |
| Carbon Dioxide | 15.0 | 11.2 | 11.2 | 23.8 | 1.5 | 5.3 | 0.8 | 45.2 | 1.0 |

TABLE 1

Gas stream composition, sulfur solubility evolution along membrane separation as depicted in U.S. Pat. No. 6,565,626 in accordance with embodiments of the present invention

| | Stream | | | | | | | | |
|---|---|---|---|---|---|---|---|---|---|
| | 201 | 202 | 203 | 204 | 205 | 206 | 207 | 208 | 209 |
| Flow (MMscfd) | 10 | 14.2 | 14.2 | 6.2 | 8 | 1.2 | 6.8 | 3.2 | 3.0 |
| Temp (° C.) | 50 | 38 | 25 | 16 | 7 | 4 | 2 | 13 | 10 |
| Pressure (psia) | 200 | 200 | 1,200 | 200 | 1,200 | 1,200 | 20 | 200 | 200 |
| Nitrogen (mol %) | 5 | 5.3 | 5.3 | 7.4 | 3.7 | 6.5 | 3.2 | 8.8 | 5.8 |
| Methane (mol %) | 80 | 83.5 | 83.5 | 68.9 | 94.8 | 88.2 | 96.0 | 46.0 | 93.2 |
| Carbon Dioxide (mol %) | 15 | 11.2 | 11.2 | 23.8 | 1.5 | 5.3 | 0.8 | 45.2 | 1.0 |
| Maximal Sulfur Contents (mg/Nm$^3$) | 0.0698 | 0.0169 | 0.0210 | 0.00094 | 0.00458 | .00016 | 0.0031 | 0.0029 | 0.00039 |
| Maximal Sulfur Flow (g/d) | 19.77 | 6.80 | 8.44 | 0.16 | 1.03 | 0.005 | 0.605 | 0.262 | 0.0338 |

TABLE 2

Gas stream composition, sulfur solubility evolution along membrane separation as depicted in U.S. Pat. No. 6,565,626 where CO$_2$ is replaced by H$_2$S and assuming similar permeability for H$_2$S and CO$_2$ in accordance with embodiments of the present invention

| | Stream | | | | | | | | |
|---|---|---|---|---|---|---|---|---|---|
| | 201 | 202 | 203 | 204 | 205 | 206 | 207 | 208 | 209 |
| Flow (MMscfd) | 10 | 14.2 | 14.2 | 6.2 | 8 | 1.2 | 6.8 | 3.2 | 3.0 |
| Temp (° C.) | 50 | 38 | 25 | 16 | 7 | 4 | 2 | 13 | 10 |
| Pressure (psia) | 200 | 200 | 1,200 | 200 | 1,200 | 200 | 1,200 | 20 | 200 |
| Nitrogen (mol %) | 5 | 5.3 | 5.3 | 7.4 | 3.7 | 6.5 | 3.2 | 8.8 | 5.8 |
| Methane (mol %) | 80 | 83.5 | 83.5 | 68.9 | 94.8 | 88.2 | 96.0 | 46.0 | 93.2 |
| Hydrogen sulfide (mol %) | 15 | 11.2 | 11.2 | 23.8 | 1.5 | 5.3 | 0.8 | 45.2 | 1.0 |
| Maximal Sulfur Contents (mg/Nm$^3$) | 3.55 | 1.55 | 1.94 | 1.12 | 0.11 | 0.12 | 0.05 | 1.52 | 0.03 |
| Sulfur Flow (g/d) | 1004 | 622 | 780 | 197 | 25 | 4.3 | 9.4 | 138 | 2.9 |

As shown in Table 1 and Table 2, sulfur contained in natural gas could depose in the membrane module due to the changes in gas composition, pressure, and temperature, which are intrinsic changes in the membrane separation process. Indeed, retentate and permeate streams exhibit lower solubility than feed and it is believed that this phenomenon leads to sulfur deposition within the membrane system resulting either in a blockage or membrane module breakage and finally discontinuity in the operation. To overcome this problem, it was discovered that a pre-conditioning of the gas by flowing the gas in sulfur solvent contactor will prevent both sulfur deposit and loss of production. As a consequence of using the methods of the present invention, the gas separation by membrane technology is more reliable and offer higher life expectancy.

As shown in Tables 1 and 2, for lower and higher dissolved sulfur concentrations in the natural gas stream, coalescing filters, which are typically used in membrane gas separation processes, are not enough to prevent sulfur deposition within the membrane system. The pre-conditioning of the gas by flowing the gas in sulfur solvent contactor coupled with coalescing filter preconditioning will prevent both sulfur deposit and loss of production due to solubility evolution along the membrane separation process. As indicated previously, major advantages of using the processes of the present invention are that the sour natural gas separation by membrane technology is more reliable and offers a higher life expectancy.

Although the present invention has been described in detail, it should be understood that various changes, substitutions, and alterations can be made hereupon without departing from the principle and scope of the invention. Accordingly, the scope of the present invention should be determined by the following claims and their appropriate legal equivalents.

The singular forms "a", "an" and "the" include plural referents, unless the context clearly dictates otherwise.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

Throughout this application, where patents or publications are referenced, the disclosures of these references in their entireties are intended to be incorporated by reference into this application, in order to more fully describe the state of the art to which the invention pertains, except when these reference contradict the statements made herein.

That which is claimed is:

1. A method of removing sulfur from a gas stream comprising the steps of:
   a. cooling the gas stream to produce a gas stream without liquids and a chilled solvent;
   b. contacting the gas stream without liquid with the chilled solvent to selectively absorb at least a portion of elemental sulfur from the gas stream;
   c. contacting the chilled solvent with an absorbent bed or a filter to remove sulfur in excess of solubility;
   d. analyzing a sulfur concentration in the gas stream without liquids to determine if the sulfur concentration exceeds a sulfur solubility estimated in retentate and permeate flows by a membrane separation process simulation; and
   e. passing the gas stream without liquids through gas separation membranes.

2. The method of claim 1 where the absorbent bed contains activated carbon, supported metallic oxides, supported organic oxides, or combinations thereof.

3. The method of claim 1 where the filter contains supported metallic filters, supported organic filters, polymeric filters, or combinations thereof.

4. The method of claim 1 where the solvent is polyethylene glycol, ethers of polyethylene glycol, polypropylene glycol, ethers of propylene glycol, n-methylpyrolidone, n-ethyl pyrolidone, n-cyclohexyl pyrolidone, n-phenyl morpholine, n-cyclohexyl morpholine, dimethyl disulfur, dimethyl-sulfur, carbon disulfide, xylene, toluene, BTX (a mixture of benzene, toluene, and xylenes), kerosene, naphthalene, alkyl-naphthalene, or combinations thereof.

5. The method of claim 1 further including the step of separating a heavy hydrocarbon stream from the gas stream without liquids prior to passing the gas stream without liquids through gas separation membranes.

* * * * *

UNITED STATES PATENT AND TRADEMARK OFFICE
CERTIFICATE OF CORRECTION

PATENT NO. : 8,801,832 B2
APPLICATION NO. : 14/178936
DATED : August 12, 2014
INVENTOR(S) : Milind M. Vaidya et al.

It is certified that error appears in the above-identified patent and that said Letters Patent is hereby corrected as shown below:

In the Claims

In Column 12, Line 18, Claim 4, the word "n-methylpyrolidone" should read --n-methyl pyrolidone--.

Signed and Sealed this
Twenty-eighth Day of October, 2014

Michelle K. Lee
*Deputy Director of the United States Patent and Trademark Office*